United States Patent
Berry et al.

(10) Patent No.: US 10,030,211 B2
(45) Date of Patent: Jul. 24, 2018

(54) METHODS FOR THE SEPARATION OR PURIFICATION OF VITAMIN E, TOCOPHEROLS AND TOCOTRIENOLS FROM LIPID MIXTURES

(71) Applicant: INVENTURE RENEWABLES, INC., Tuscaloosa, AL (US)

(72) Inventors: William W. Berry, Tuscaloosa, AL (US); William Rusty Sutterlin, Tuscaloosa, AL (US); Mark G. Tegen, Tuscaloosa, AL (US); Ryan Long, Tuscaloosa, AL (US)

(73) Assignee: Inventure Renewables, INC., Tuscaloosa, AL (US)

(*) Notice: Subject to any disclaimer, the term of this patent is extended or adjusted under 35 U.S.C. 154(b) by 0 days.

(21) Appl. No.: 14/913,622

(22) PCT Filed: Aug. 29, 2014

(86) PCT No.: PCT/US2014/053594
§ 371 (c)(1),
(2) Date: Feb. 22, 2016

(87) PCT Pub. No.: WO2015/050655
PCT Pub. Date: Apr. 9, 2015

(65) Prior Publication Data
US 2016/0200701 A1   Jul. 14, 2016

Related U.S. Application Data

(60) Provisional application No. 61/872,354, filed on Aug. 30, 2013, provisional application No. 61/990,052, filed on May 7, 2014.

(51) Int. Cl.
*C11B 3/00* (2006.01)
*B01D 3/10* (2006.01)
(Continued)

(52) U.S. Cl.
CPC ............... *C11B 3/00* (2013.01); *B01D 3/10* (2013.01); *C07C 67/02* (2013.01); *C07D 311/72* (2013.01);
(Continued)

(58) Field of Classification Search
CPC .. C07D 31/72; C11B 3/00; C11B 3/12; C11B 1/10; C07C 67/02; C07C 67/03; C07C 67/08; C11C 3/003; B01D 3/10
See application file for complete search history.

(56) References Cited

U.S. PATENT DOCUMENTS 4,032,550 A * 6/1977 White ............... B01J 37/00
554/165
5,190,618 A * 3/1993 Top ............... C07D 311/72
159/49
(Continued)

FOREIGN PATENT DOCUMENTS

GB      546865 A * 8/1942 .......... A61K 31/355

OTHER PUBLICATIONS

Fang, T., et al., Supercritical methanol process of modifying oil byproduct for concentrating natural tocopherols, 2007, Ind. ENg. Chem. Res., vol. 46, No. 16, pp. 5325-5332 (Year: 2007).*
(Continued)

*Primary Examiner* — Yate' K Cutliff
(74) *Attorney, Agent, or Firm* — Greer, Burns & Crain; Gregory P. Einhorn

(57) ABSTRACT

This invention generally relates to the isolation of molecules exhibiting vitamin E activity, e.g. tocopherols and/or tocotrienols, from mixed lipid feedstocks. In alternative embodiments, the inventions provides methods and industrial processes for isolating vitamin E molecules, including tocopherols and/or tocotrienols, from mixed lipid feedstocks by combining the feedstock with an alcohol and reacting the mixture at or above the critical point of the alcohol, and then optionally separating the products into discreet fractions.

20 Claims, 3 Drawing Sheets

(51) Int. Cl.
*C11B 3/06* (2006.01)
*C11C 3/00* (2006.01)
*C07C 67/02* (2006.01)
*C07D 311/72* (2006.01)
*C11B 3/12* (2006.01)

(52) U.S. Cl.
CPC .................................... *C11B 3/06* (2013.01); *C11B 3/12* (2013.01); *C11C 3/003* (2013.01)

(56) References Cited

U.S. PATENT DOCUMENTS

| | | | | |
|---|---|---|---|---|
| 5,424,457 A | * | 6/1995 | Sumner, Jr. | C07J 9/00 |
| | | | | 549/408 |
| 5,627,289 A | * | 5/1997 | Jeromin | A23L 3/3544 |
| | | | | 549/413 |
| 2001/0044548 A1 | | 11/2001 | May et al. | |

OTHER PUBLICATIONS

Fang et al., "Supercritical Methanol Process of Modifying Oil Byproduct for Concentrating Natural Tocopherols" Ind. Eng. Chem. Res. 2007, v 46, p. 5325-5332.

Young, International Search Report and Written Opinion for PCT/US2014/053594 dated Mar. 11, 2015.

\* cited by examiner

METHODS FOR THE SEPARATION OR PURIFICATION OF VITAMIN E, TOCOPHEROLS AND TOCOTRIENOLS FROM LIPID MIXTURES

RELATED APPLICATIONS

This application is a national phase application claiming benefit of priority under 35 U.S.C. § 371 to Patent Convention Treaty (PCT) International Application serial no. PCT/US2014/053594, filed Aug. 29, 2014, which claims the benefit of priority under 35 U.S.C. § 119(e) of U.S. Provisional Application Ser. No. (U.S. Ser. No. ). 61/990,052, filed May 7, 2014; and U.S. Ser. No. 61/872,354, filed Aug. 30, 2013. The aforementioned applications are expressly incorporated herein by reference in their entirety and for all purposes.

FIELD OF THE INVENTION

This invention generally relates to the preparation of, and optionally also the separation of, molecules exhibiting vitamin E activity, including unesterified (free) tocopherols and/or tocotrienols, from mixed lipid feedstocks. In alternative embodiments, the invention provides methods and industrial processes for processing mixed lipid feedstocks to generate a reaction product comprising substantially unesterified (or free) tocopherols and/or tocotrienols, and if present, sterols, by combining a feedstock having unesterified (or free) tocopherols and/or tocotrienols, as well as various lipids e.g. free fatty acids and esters of fatty acids e.g. glycerides, tocopherol esters, sterol esters, or any combination thereof, with an alcohol and reacting the mixture at or above the critical point of the alcohol at sufficient temperature and pressure, and then optionally separating or isolating the reacted and unreacted products.

BACKGROUND OF THE INVENTION

Tocopherols are a group of methylated phenol compounds exhibiting vitamin E activity, found in small quantities in animal and vegetable fats. The group of compounds includes alpha, beta, gamma, and delta tocopherol, as well as alpha, beta, gamma, and delta tocotrienol. Tocopherols have a number of commercial applications, primarily as a vitamin E dietary supplement. Other commercial applications include use as a food additive to prevent spoilage and oxidation.

Tocopherols are present in very small quantities in crude vegetable oils. The majority of the tocopherols contained in the crude fats are removed during the deodorization stage of the refining process. The resulting deodorizer distillate streams typically contain from less than 1% to greater than 20% tocopherols by volume. The remaining volume is comprised of a combination of various lipid derivatives, including tocopherol esters, free fatty acids, sterols and sterol esters, hydrocarbons such as squalene, as well as small quantities of glycerides. Because tocopherols represent such a significant commercial value, complicated chemical methods for their removal and purification from deodorizer distillate streams are currently utilized despite their high cost and level of complexity.

Methods of tocopherol purification in the art involve multi-step processes and require a catalyst, solvent, or both, in order to concentrate and isolate tocopherols from deodorizer distillates. Further, prior methods require long residence times for various reactions to take place, followed by a complicated series of distillations or separations to isolate the tocopherol products from the distillate.

SUMMARY OF THE INVENTION

In alternative embodiments, the invention provides methods and industrial processes for esterifying organic acids and trans-esterifying esters in a mixed lipid feedstock, the processes and method comprising:

(a) providing the mixed lipid feedstock comprising unesterified (or free) tocopherol and/or unesterified tocotrienol molecules, and esters of fatty acids wherein optionally the tocopherol comprises alpha-tocopherol, beta-tocopherol, gamma-tocopherol, delta-tocopherol or a combination thereof, and optionally the tocotrienol comprises alpha-tocotrienol, beta-tocotrienol, gamma-tocotrienol, delta-tocotrienol or a combination thereof; and (b) combining or feeding the mixed lipid feedstock with an alcohol to form a mixture, wherein optionally the alcohol comprises at least about 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, or 40% or more wt %, of the feedstock, or between about 0.5% and 50% wt %, of the feedstock, or between about 1% and 40% wt %, of the feedstock, or, the amount of alcohol in the mixture can be in the range of between about 1 mol to about 100 mol per mol of feedstock, e.g. between about 10 mol to about 90 mol per mol of feedstock, about 20 mol to about 80 mol per mol of feedstock, about 30 mol to about 70 mol per mol of feedstock, or about 40 mol to about 60 mol per mol of feedstock, and wherein optionally the combining or feeding step comprises feeding the mixture into a reactor or a reaction vessel as a continuous process, and optionally the reactor or reaction vessel is purged with nitrogen prior to the feedstock and alcohol entering the reactor;

(c) reacting the mixture at a temperature and pressure sufficient to cause the alcohol to become supercritical or near supercritical alcohol (to generate an alcohol at a supercritical state or an alcohol partially or substantially as a supercritical fluid), thereby substantially esterifying the organic acids and substantially transesterifying the esters in the mixture, but leaving the free (unesterified) tocopherol and/or the free (unesterified) tocotrienol molecules substantially unreacted (substantially unesterified), and, if present, leaving the free (unesterified) sterols in the feedstock substantially unreacted (substantially unesterified), thereby generating a reacted reaction mixture comprising reaction products comprising unesterified (or free) tocopherol and/or tocotrienol molecules, and if present, unesterified (or free) sterols, and fatty acid alkyl esters, wherein: substantially all of the organic acids are esterified, and substantially all of the tocopherol and/or tocotrienol molecules are unesterified, and if sterols are present, substantially all of the sterols are unesterified, wherein optionally the alcohol is methanol and the fatty acid alkyl esters comprise fatty acid methyl esters (FAME), and optionally the reaction mixture comprises reaction products and unreacted products comprising free sterols, sterol esters, free fatty acids, glycerides, hydrocarbons, squalene or any combination thereof, and optionally the glycerides comprise a mono-, di-, and/or tri-glyceride, and optionally the mixture is reacted at a temperature in a range of between about 150° C. and about 300° C., or in a range of between about 100° C. and about 350° C., and optionally the mixture is reacted at a pressure in the range of between about 500 psi to about 3000 psi, or, the mixture is reacted at a pressure slightly in excess of the vapor pressure of the alcohol at a selected operating temperature, and optionally the pressure is about 1, 2, 3, 4, 5, 6, 7, 8, 9, 10, 11, 12, 13, 14, 15, 16, 17, 18 19 or 20 psi or more, or between about 5 to 50 psi or more, over the vapor pressure of the alcohol, and optionally substantially all is equivalent to 90%, 91%, 92%, 93%, 94%, 95%, 96%, 97%, 98%, 99%, 99.5%, 99.8% or more %.

In alternative embodiments, the processes and methods of the invention further comprise separating isolating, or purifying the reaction products in the reaction mixture into fractions such that the tocopherol and/or the tocotrienol are separated, isolated or purified into a fraction separate (discreet) from the remaining reaction products or unreacted products; and optionally the free sterol, the sterol ester, the free fatty acid, the glyceride (e.g. mono-, di-, and/or tri-glyceride), the hydrocarbon or squalene are also separated, isolated or purified into discreet fractions.

In alternative embodiments, the feedstock comprises vitamin E, an unesterified tocopherol or tocotrienol, esters of the tocopherol or tocotrienol, or any combination thereof. The feedstock can comprise free (unesterified) tocopherols, free (unesterified) tocotrienols, tocopherol esters, tocotrienol esters, free sterols, sterol esters, free fatty acids, glycerides, e.g. mono-, di-, and/or tri-glycerides, hydrocarbons, squalene, or any combination thereof.

In alternative embodiments, the feedstock comprises: unesterified tocopherol or tocotrienol molecules in the range of between about less than 1 wt % to less than about 25 wt %, or in the range of between about 0.5% and 30% wt % or between about 1% and 25% wt %, or between about 1 wt % and 35 wt % of the feedstock, or about 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29% or 30% or more wt %, of the feedstock.

In alternative embodiments, the separated, isolated or purified reaction products, or the discreet fractions, comprise separated, isolated or purified free tocopherols, free tocotrienols, free sterols, fatty acid alkyl esters, glycerol, squalene, or any combination thereof, and optionally the separated, isolated or purified tocopherols or tocotrienols comprises one, several or all of the four tocopherols (alpha, beta, gamma, delta) and/or four tocotrienols (alpha, beta, gamma, delta).

In alternative embodiments, the separated, isolated or purified reaction products, or the discreet fractions, comprise one reaction product, or substantially one reaction product, at about 99.5%, 99%, 98%, 97%, 96%, 95%, 94%, 93%, 92%, 91% or 90% purity.

In alternative embodiments, the mixture is reacted at a temperature in a range of between about 150° C. and about 300° C. and a pressure in a range of between about 500 psi to about 3000 psi; or, in a range of between about 100° C. and about 350° C. and a pressure in a range of between about 500 psi to about 3000 psi.

In alternative embodiments, the mixture is reacted for a time period in the range of between about 0 minutes to about 120 minutes, or between about 1 to 100 minutes.

In alternative embodiments, wherein the alcohol has between 1 and 5 carbons, or the alcohol has 1, 2, 3, 4, 5, 6, or 7 or more carbons; or, the alcohol comprises a methanol, or the alcohol is selected from the group consisting of an ethanol, a butanol, an isopropyl alcohol, a sec-butanol, a t-butanol, a benzyl alcohol, or a combination thereof.

In alternative embodiments, the mixed lipid feedstock comprises a deodorizer distillate, or a vegetable oil deodorizer distillate (a distillate of a vegetable oil deodorization process); and, the deodorizer distillate (or distillate of a vegetable oil deodorization process) can be derived from a soybean oil, a canola oil, a rapeseed oil, a sunflower oil, a rice bran oil, an algae oil, a jatropha oil, a corn oil, a camelina oil, or a safflower oil. The mixed lipid feedstock can comprise a fatty acid distillate, or, the fatty acid distillate can be derived from palm oil.

In alternative embodiments, the invention provides methods and industrial processes for recovering or separating tocopherols, tocotrienols, or both from a mixed lipid feedstock, the method or industrial process comprising:

(a) combining the mixed lipid feedstock with an alcohol to form a reaction mixture, wherein the mixed lipid feedstock comprises tocopherols and/or tocotrienols, sterols, free fatty acids and glycerides, and optionally tocopherol and/or tocotrienol esters and sterol esters, or any combination thereof, wherein optionally the alcohol comprises at least about 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, or 40% or more wt %, of the feedstock, or between about 0.5% and 50% wt %, of the feedstock, or between about 1% and 40% wt %, of the feedstock, or, the amount of alcohol in the mixture can be in the range of between about 1 mol to about 100 mol per mol of feedstock, e.g. between about 10 mol to about 90 mol per mol of feedstock, about 20 mol to about 80 mol per mol of feedstock, about 30 mol to about 70 mol per mol of feedstock, or about 40 mol to about 60 mol per mol of feedstock;

(b) forming a reacted reaction mixture comprising reaction products by reacting the reaction mixture:

(1) at a temperature in the range of between about 150 degrees Celsius to about 300 degrees Celsius, or in the range of between about 100° C. and about 350° C., and at a pressure in the range of between about 1,000 psi to about 3,000 psi, or the mixture is reacted at a pressure in the range of between about 500 psi to about 3000 psi, or, the mixture is reacted at a pressure slightly in excess of the vapor pressure of the alcohol at a selected operating temperature, and optionally the pressure is about 1, 2, 3, 4, 5, 6, 7, 8, 9, 10, 11, 12, 13, 14, 15, 16, 17, 18 19 or 20 psi or more, or between about 5 to 50 psi or more, over the vapor pressure of the alcohol; or (2) a temperature and pressure sufficient to generate a supercritical or near supercritical alcohol (the alcohol reaches a supercritical state or partially or substantially becomes a supercritical fluid), thereby:

i. converting substantially all of the tocopherol esters and/or tocotrienol esters to: free (unesterified) tocopherols and/or free (unesterified) tocotrienols, and fatty acid alkyl esters, ii. converting the sterol esters to sterols and fatty acid alkyl esters, iii. converting the glycerides to fatty acid alkyl esters and glycerol, iv. converting the free fatty acids to fatty acid alkyl esters; and v. leaving the free (unesterified) tocopherols, free (unesterified) tocotrienols and, if present, free (unesterified) sterols in the feedstock substantially unreacted (substantially unesterified), thereby generating reaction products comprising: free (unesterified) tocopherols and/or free (unesterified) tocotrienols, free (unesterified) sterols, and fatty acid alkyl esters, and optionally substantially all is equivalent to 90%, 91%, 92%, 93%, 94%, 95%, 96%, 97%, 98%, 99%, 99.5%, 99.8% or more %; and (c) separating or recovering the substantially unesterified tocopherols and/or tocotrienols from the reaction mixture.

In alternative embodiments, the feedstock comprises free tocopherols, free tocotrienols, tocopherol esters, tocotrienol esters, free sterols, sterol esters, free fatty acids, glycerides, e.g. mono-, di-, and/or tri-glycerides, hydrocarbons, e.g. squalene, or any combination thereof. The feedstock can comprise tocopherols and/or tocotrienols in a range of between about less than 1 wt % to about 25 wt %, or between about 1 wt % and 30 wt %, or about 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29% or 30% or more wt %, of the feedstock. In alternative embodiments, the reaction product mixture comprises free tocopherols, free tocotrienols, free sterols, fatty acid alkyl esters, glycerol, squalene, or any combination thereof.

In alternative embodiments, the mixture is reacted at a temperature in the range of between about 150° C. and about 300° C., or in the range of between about 100° C. and about 350° C., and a pressure in the range of between about 500 psi to about 3000 psi.

In alternative embodiments, the mixture is reacted for a time period in the range of between about 0 minutes to about 120 minutes, or between about 1 minute and about 100 minutes.

In alternative embodiments, the alcohol has between 1 and 5 carbons, or the alcohol has 1, 2, 3, 4, 5, 6, or 7 or more carbons; or, the alcohol is selected from the group consisting of a methanol, an ethanol, a butanol, an isopropyl alcohol, a sec-butanol, a t-butanol, a benzyl alcohol and a combination thereof.

In alternative embodiments, the mixed lipid feedstock is a deodorizer distillate, or a vegetable oil deodorizer distillate (a distillate of a vegetable oil deodorization process). The deodorizer distillate (or distillate of a vegetable oil deodorization process) can be derived from a soybean oil, a canola oil, a rapeseed oil, a sunflower oil, a rice bran oil, a safflower oil or a mixture thereof. The mixed lipid feedstock can be a fatty acid distillate. The fatty acid distillate can be derived from a palm oil.

In alternative embodiments, methods and industrial processes comprising:

(a) providing a reaction mixture comprising an alcohol and a mixed lipid feedstock comprising unesterified (free) tocopherols or unesterified (free) tocotrienols, and lipids, wherein optionally the tocopherol comprises alpha-tocopherol, beta-tocopherol, gamma-tocopherol, delta-tocopherol or a combination thereof, and optionally the tocotrienol comprises alpha-tocotrienol, beta-tocotrienol, gamma-tocotrienol, delta-tocotrienol or a combination thereof, wherein optionally the alcohol comprises at least about 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, or 40% or more wt %, of the feedstock, or between about 1% and 40% wt %, of the feedstock, or, the amount of alcohol in the mixture can be in the range of between about 1 mol to about 100 mol per mol of feedstock, e.g. between about 10 mol to about 90 mol per mol of feedstock, about 20 mol to about 80 mol per mol of feedstock, about 30 mol to about 70 mol per mol of feedstock, or about 40 mol to about 60 mol per mol of feedstock; and (b) reacting the reaction mixture at a temperature in the range of between about 100° C. and about 350° C. and at a pressure in the range of between about 1,000 psi to about 3,000 psi, thereby: esterifying or trans-esterifying substantially all of the lipids to generate fatty alky esters; and leaving the unesterified (free) tocopherols, and if present the unesterified (free) sterols, substantially unreacted (unesterified).

In alternative embodiments the feedstock comprises free tocopherols, free tocotrienols, tocopherol esters, tocotrienol esters, free sterols, sterol esters, free fatty acids, glycerides, e.g. mono-, di-, and/or tri-glycerides, hydrocarbons, e.g. squalene, or any combination thereof. The feedstock can comprise tocopherols and/or tocotrienols in a range of between about less than 1 wt % to about 25 wt %, or between about 1 wt % and 35 wt % of the feedstock, or about 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29% or 30% or more wt %, of the feedstock.

In alternative embodiments, the mixture is reacted for a time period in the range of between about 0 minutes to about 120 minutes, or between about 1 minute and about 100 minutes.

In alternative embodiments, the alcohol has between 1 and 5 carbons, or the alcohol has 1, 2, 3, 4, 5, 6, or 7 or more carbons; or, the alcohol is selected from the group consisting of a methanol, r an ethanol, a butanol, an isopropyl alcohol, a sec-butanol, a t-butanol, a benzyl alcohol and a combination thereof.

In alternative embodiments the mixed lipid feedstock is a deodorizer distillate, or a vegetable oil deodorizer distillate (a distillate of a vegetable oil deodorization process). The deodorizer distillate (or distillate of a vegetable oil deodorization process) can be derived from a soybean oil, a canola oil, a rapeseed oil, a sunflower oil, a rice bran oil, a safflower oil or a mixture thereof. The mixed lipid feedstock can be a fatty acid distillate. The fatty acid distillate can be derived from a palm oil.

In alternative embodiments, the invention provides methods and industrial processes substantially as hereinbefore described, or as substantially described in FIG. 1 or FIG. 2. In alternative embodiments, the invention provides a method or an industrial process comprising a process as set forth in FIG. 1 or FIG. 2.

In alternative embodiments, the object of the present invention is to provide methods and industrial processes for the economically efficient purification or separation, and optionally the isolation or purification of free (unesterified) tocopherols and/or tocotrienols (and if present, free (unesterified) sterols) from mixed lipid feedstocks comprising tocopherols and/or tocotrienols, such as: natural oil distillate feedstocks such as those produced during a processing step in natural oil refining wherein the object of the processing step is to remove fatty acids from the crude oil; or, deodorizer distillate streams produced during the refining of natural oils or fats; or, fatty acid distillate streams produced during the refining of natural oils or fats.

All publications, patents, patent applications cited herein are hereby expressly incorporated by reference for all purposes.

Reference will now be made in detail to various exemplary embodiments of the invention. The following detailed description is provided to give the reader a better understanding of certain details of aspects and embodiments of the invention, and should not be interpreted as a limitation on the scope of the invention.

DETAILED DESCRIPTION OF THE INVENTION

In alternative embodiments, the invention provides processes for the preparation of, and optionally concentration or isolation of, molecules having vitamin E activity, including free or unesterified tocopherols and tocotrienols, as well as sterols, lipids, lipid derivatives, and various hydrocarbons, from mixed lipid feedstocks, including animal and vegetable oils. In alternative embodiments, the mixed lipid feedstocks comprise deodorizer distillate streams produced during the refining of natural fats or oils. In alternative embodiments, all vitamin E components, including four tocopherols (alpha, beta, gamma, delta) and four tocotrienols (alpha, beta, gamma, delta), and any homologues thereof exhibiting vitamin E activity, are prepared, and optionally isolated, using the processes of this invention. In alternative embodiments, the feedstock comprises tocopherols but not tocotrienols. In alternative embodiments, the feedstock comprises tocotrienols but not tocopherols. In alternative embodiments, the feedstock comprises some combination of tocopherols and tocotrienols. In alternative embodiments, processes of the invention are more economical and efficient than currently used approaches for the generation, concentration (and optionally, the isolation) of free (unesterified) tocopherols from feedstocks such as deodorizer distillates or natural oil distillate feedstocks.

When referred to in the present disclosure, a "free tocopherol" or "free sterol" is a tocopherol or sterol molecule with no fatty acid ester moiety. This is necessary to distinguish those tocopherol or sterol derivatives with a fatty acid ester moiety, e.g. tocopherol esters, which are present in the feedstock in various embodiments of the present invention. It is common for esters such as tocopherol esters and sterol esters to form in a distillate derived from a vegetable oil due to the presence of free fatty acids in the distillate product. When allowed to sit in storage, free fatty acids in the crude distillate tend to esterify a portion of the tocopherols and sterols, thereby generating some quantity of tocopherol and sterol esters.

When referred to herein, "tocopherols" or "free tocopherols" may include any molecules that exhibit vitamin E activity including, without limitation, tocopherols and tocotrienols, e.g. alpha-tocopherol, beta-tocopherol, gamma-tocopherol, delta-tocopherol, alpha-tocotrienol, beta-tocotrienol, gamma-tocotrienol, delta-tocotrienol, or any combination thereof.

Figure 1:
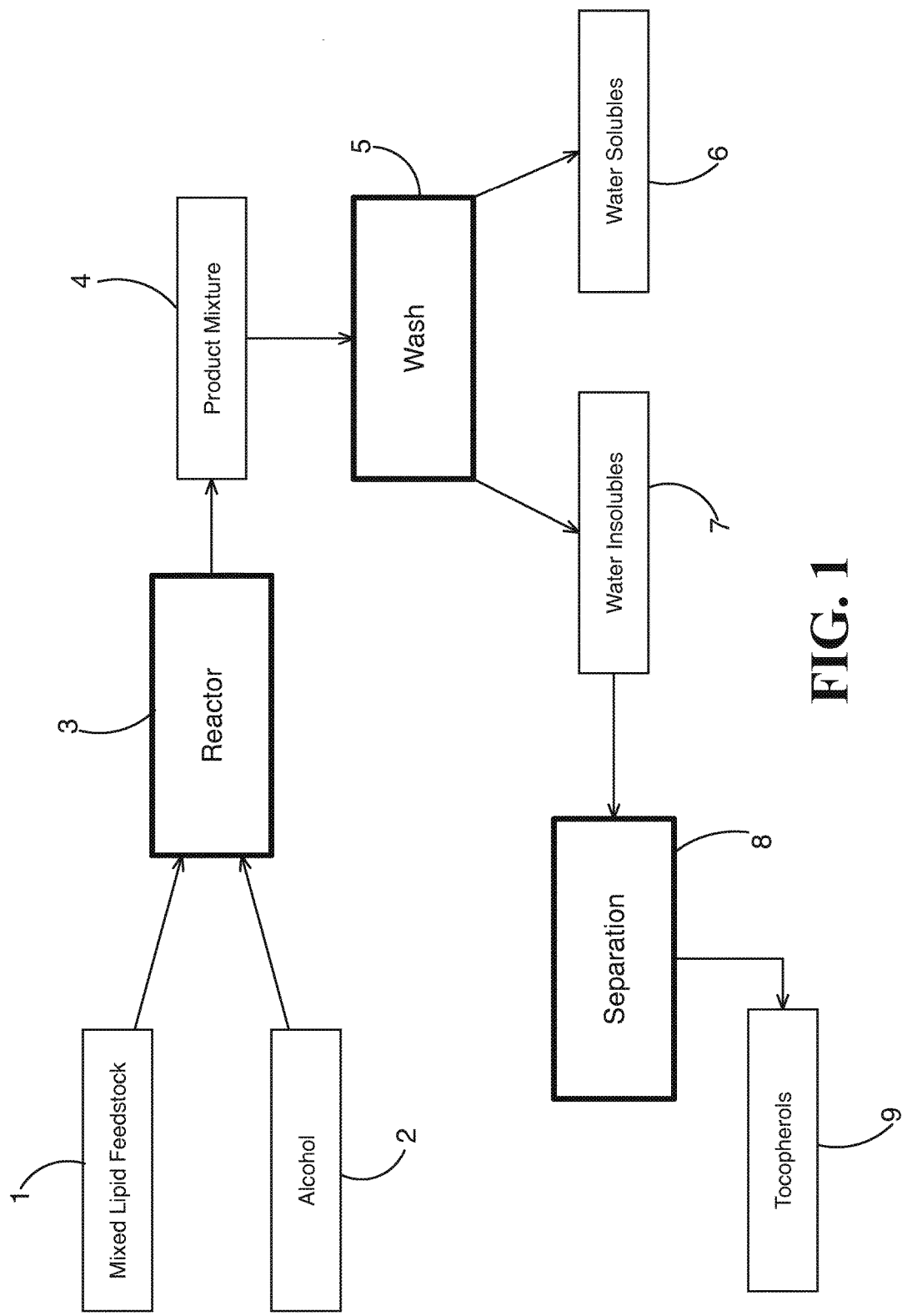
FIG. 1 and FIG. 2 are schematic diagrams of exemplary methods of the invention comprising isolating, purifying or separating tocopherols, tocotrienols and other molecules, as described below, from mixed lipid streams or equivalents thereof.
Figure 2:
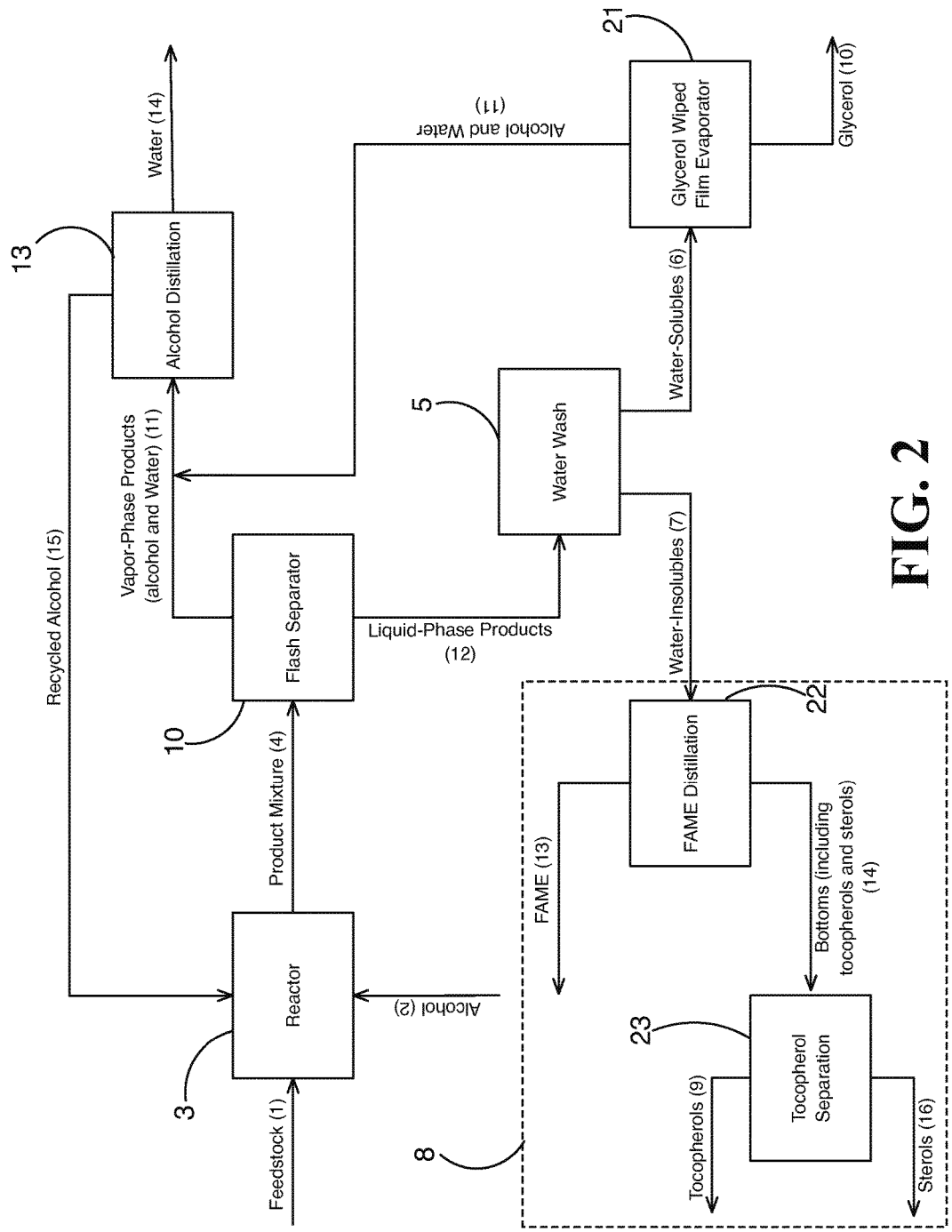

The present disclosure provides alternative embodiments of methods and industrial processes for the isolation of tocopherols from mixed lipid streams. In alternative embodiments, methods of the invention comprise a single reaction step that does not rely on the use of chemical catalysts, acids, or bases. In alternative embodiments (as illustrated in FIG. 1 or FIG. 2) a mixed lipid feedstock 1 comprising tocopherols (including unesterified tocopherols and optionally esterified tocopherols) is first combined with an alcohol 2 to form a mixture. The mixture is then reacted in a heated and pressurized reactor 3 at conditions near, at, or above the critical point of the alcohol. In alternative embodiments the mixture is reacted at a temperature and pressure sufficient to cause the alcohol to become supercritical or near supercritical, i.e., to generate an alcohol at a supercritical state or an alcohol partially or substantially as a supercritical fluid.

In various embodiments, the reaction generates primarily a product mixture 4 of free (unesterified) tocopherols, free sterols, fatty acid alkyl esters, glycerol or a combination thereof.

In certain embodiments, the reaction mixture is then transferred to a washing unit 5 wherein the water-soluble materials 6, e.g. glycerol, are separated from the reaction mixture. The remaining water-insoluble materials 7, wherein the free tocopherols are included, are then transferred to a separation unit or system 8 wherein the remaining components of the reaction mixture are separated from the free tocopherols (\9 through any one of several suitable methods known in the art, e.g. distillation, crystallization, or other suitable techniques, or an combination of techniques known in the art.

In alternative embodiments, the feedstock is a mixture of lipid and lipid derivatives comprising tocopherols. In certain embodiments, the feedstock is a deodorizer distillate produced during the chemical refining of a vegetable oil, e.g. soybean oil, canola oil, rapeseed oil, sunflower oil, bran oil. In other embodiments, the feedstock is a fatty acid distillate produced during the physical refining of vegetable oils, e.g. palm oil. The composition of natural oil distillates varies depending on the composition of the crude oil from which it was derived, as well as the specific processes and reaction conditions used to generate the distillate. For example, a fatty acid distillate derived from crude palm oil in the physical refining process can comprise in the range of between about less than 1% wt to about 20 wt % tocopherols, e.g. between about 0.5 wt % to about 10 wt % tocopherols, between about 10 wt % to about 95 wt % free fatty acids (FFA), e.g. between about 15 wt % to about 45 wt %, or about 25 wt % to about 35 wt % FFA, between about 1 wt % to about 60 wt % glycerides, e.g. between about 10 wt % to about 50 wt %, about 15 wt % to about 40 wt %, or about 25 wt % to about 35 wt % glycerides, between about 1 wt % sterols to about 40 wt % sterols, e.g. between about 5 wt % sterols to about 30 wt % sterols, about 10 wt % to about 25 wt % sterols, or about 15 wt % to about 20 wt % sterols, between about less than 0.01 wt % water to about 0.5 wt % water, as well as small quantities, e.g.

between about less than 1 wt % and about 5 wt % each, of tocopherol esters, sterol esters, and various hydrocarbons such as squalene.

In alternative embodiments, the feedstock is a tocopherol-containing distillate produced during the chemical refining of a crude vegetable oil. In alternative embodiments, the feedstock is a soybean oil fatty acid distillate (SFAD). The SFAD can be comprised of, for example, between about less than 1 wt % tocopherols to about 20 wt % tocopherols, e.g. between about 2 wt % to about 18 wt %, about 4 wt % to about 16 wt %, about 6 wt % to about 14 wt %, about 8 wt % to about 12 wt %, or about 10 wt % tocopherols, between about 2 wt % to about 30 wt % sterols, e.g. between about 5 wt % to about 25 wt %, about 10 wt % to about 18 wt % sterols, or about 17 wt % sterols, between about 10 wt % to about 50 wt % FFA, e.g. between 15 wt % to about 45 wt %, about 20 wt % to about 40 wt %, about 25 wt % to about 35 wt %, or about 30 wt % FFA, between about 1 wt % to about 60 wt % glycerides, e.g. between about 10 wt % to about 50 wt %, about 15 wt % to about 40 wt %, or about 25 wt % to about 35 wt % glycerides, as well as small quantities, e.g. between about less than 1 wt % and about 5 wt % each of, tocopherol esters, sterol esters, and various hydrocarbons such as squalene.

In alternative embodiments, the feedstock used in the various exemplary processes of the invention comprises a distillate produced during the refining of a natural oil, e.g. a distillate produced during a step in a natural oil refining processes, e.g. the chemical natural oil refining process or the physical natural oil refining process, that is used to remove the majority of the free fatty acids from the crude oil, and comprises a mixture of free tocopherols, and/or tocotrienols as well as other lipid derivatives, e.g. free sterols, tocopherol esters, sterol esters, glycerides, free fatty acids, hydrocarbons such as squalene, or any combination thereof. However, the feedstock used in the various embodiments of the present invention is not limited to vegetable oil distillates. In alternative embodiments suitable feedstocks include any lipid mixture comprising tocopherols and esterified compounds or esters of fatty acids, e.g. tocopherol esters, such that transesterification between the alcohol and the esters present in the feedstock can occur.

The feedstock and can be derived from any natural fat source, e.g., wheat germ oil, corn oil, soybean oil, safflower oil, peanut oil, cottonseed oil, sunflower oil, rapeseed oil, palm oil, canola oil, algae oil, tallow, or other animal fat or vegetable oil product comprising tocopherols and esterified compounds. In alternative embodiments, the feedstock is from a deodorizer distillate or fatty acid distillate resulting from the deodorization step, or fatty acid removal or "striping" step of crude vegetable oil refining from (chemical or physical refining), e.g., soybean oil, palm oil, canola oil, rapeseed oil, wheat germ oil, safflower oil, peanut oil, cottonseed oil, sunflower oil, grape seed oil, jatropha oil, palm kernel oil, coconut oil, olive oil, corn oil, hazelnut oil, linseed oil, rice bran oil, safflower oil, sesame oil, algae oil, tallow or a combination thereof, or other animal or vegetable oils.

In alternative embodiments, the feedstock used in processes of the invention has been sitting for periods of time to allow for the accumulation of a sizable quantity of material before further processing takes place, to concentrate and extract tocopherols; this is common practice in the process of refining crude vegetable or animal oils. This sitting, or lag, time results in having free fatty acids present in the deodorizer distillate feedstock to esterify some of all of the tocopherols and sterols present in the mixture, resulting in the formation of tocopherol esters and sterol esters; thus, in alternative embodiments feedstock used to practice the invention comprise "free" tocopherols and sterols, tocopherol esters, sterol esters, free fatty acids, a mono-, di-, and/or tri-glycerides.

In alternative embodiments, the alcohol contains between 1 and 5 carbons, e.g. methanol, ethanol, propanol, butanol, isopropyl alcohol, sec-butanol, t-butanol, or a combination thereof. In various other embodiments, conditions may be such that a higher alcohol containing more than 5 carbons would be preferred. For purposes of this discussion, methanol is used as the alcohol, however those skilled in the art would understand that other alcohols can be used.

In alternative embodiments (see FIG. 2), a mixed lipid feedstock 1, e.g. a fatty acid distillate, and an alcohol 2 are combined to form a mixture prior to entering the reaction vessel 3. The feedstock and alcohol can be combined in such a way that the step of feeding the mixture into the reaction vessel is a continuous process. In such embodiments, the feedstock and alcohol are contained in separate vessels and maintained at a constant level. The alcohol and feedstock are then fed to a separate vessel, wherein the feedstock and alcohol are combined in the desired ratios prior to entering the reaction vessel. In alternative embodiments, the feedstock is fed to a reaction vessel comprising and alcohol in a supercritical state, such that the feedstock combines with the supercritical alcohol in the reaction vessel to form a reaction mixture.

The amount of alcohol 2 in the mixture can be in the range of between about 1 mol to about 100 mol per mol of feedstock, e.g. between about 10 mol to about 90 mol per mol of feedstock, about 20 mol to about 80 mol per mol of feedstock, about 30 mol to about 70 mol per mol of feedstock, or about 40 mol to about 60 mol per mol of feedstock.

In alternative embodiments, the methods can comprise an optional oxygen degassing step, wherein any oxygen present in the feedstock is substantially removed. Any of several known methods for oxygen degassing can be used in this step, e.g. purging the reactor with nitrogen prior to the feedstock and alcohol entering the reactor.

In alternative embodiments, after the feedstock and alcohol have been combined, the mixture is fed to the reaction vessel 3 wherein it is subjected to a temperature and pressure such that the alcohol becomes supercritical, or near supercritical. At or above the critical point of the alcohol, distinct liquid and gas phases do not exist, and the phase-boundary between liquid and gas is terminated. The temperature can be, for example, in the range of between about 150° C. to about 350° C. (degrees Celsius), between about 150° C. to about 300° C., between about 250° C. to about 300° C., between about 100° C. to about 400° C. or between about 280° C. to about 290° C., e.g. 285° C.

In various embodiments, the pressure of the reactor is slightly in excess of the vapor pressure of the alcohol of choice at the selected operating temperature, e.g., about 5, 10, 15, 20, or 25 or more psi over the vapor pressure. Maintaining the pressure of the reaction vessel above the vapor pressure of the alcohol prevents the alcohol from boiling and allows it to reach a supercritical state. The pressure for the reaction can be in the range of between about 500 psi to about 3000 psi, between about 1500 psi to about 2500 psi or, between about 1000 psi and about 2500 psi, or between about 1500 psi to about 2000 psi.

In one embodiment, the feedstock is combined with alcohol to form a starting mixture and reacted at a temperature of between about 150° C. to about 300° C., at a pressure of between about 1500 psi to about 2500 psi; and optionally, after this reaction, fatty acid esters are separated from free sterols and free tocopherols.

In alternative embodiments, the reactor is operated at a temperature above the super critical temperature of the selected alcohol. For example, when methanol is used as an alcohol, the temperature of the reactor is maintained at a temperature of at least 240° C., since the critical temperature of methanol is 240° C., or when ethanol is used as an alcohol, the temperature of the reactor is maintained at a temperature of at least 243° C., since the critical temperature of ethanol is 243° C., or when propanol is used as an alcohol, the temperature of the reactor is maintained at a temperature of at least 264° C., since the critical temperature of propanol is 264° C., or when isopropanol is used as an alcohol, the temperature of the reactor is maintained at a temperature of at least 236° C., since the critical temperature of isopropanol is 236° C., or when butanol is used as an alcohol, the temperature of the reactor is maintained at a temperature of at least 287° C., since the critical temperature of butanol is 287° C., or when isobutanol is used as an alcohol, the temperature of the reactor is maintained at a temperature of at least 275° C., since the critical temperature of isobutanol is 275° C., or when tert.-butanol is used as an alcohol, the temperature of the reactor is maintained at a temperature of at least 233° C., since the critical temperature of tert-butanol is 233° C.

In alternative embodiments, reactions conditions of processes of the invention comprise a pH of anywhere in the range of 0 to about 7, or at pH 0.5, 1, 2, 3, 4, 5, 6, 7, 7.2, 7.4 or more basic.

In alternative embodiments, the reactor system is batch or continuous. To practice this invention, any conventional pressure vessel system can be used, e.g., any system that will operate in a batch and/or a continuous mode. In alterative embodiments, a continuous pipe-type or plug-flow reactor, or equivalent, can be used to carry out a reaction of the invention. In alternative embodiments, the reactor comprises a pipe or equivalent with sufficient residence time to allow for the reaction to complete, and can be operated under varying, e.g., the appropriated and selected, temperatures and pressures. The pipe allows for a reasonable reaction to occur with minimized vessel complexity.

In alternative embodiments, the plug flow reactor comprises a pipe that is maintained at the target pressure and temperature ranges and allows the reaction mixture to pass through the internal volume of the pipe. In such a system, the reaction mixture is sent through the reactor at a constant mass flow rate, thereby exposing the reaction mixture to a constant temperature and pressure for a predetermined time. The plug flow reactor system also allows for a continuous process, as material can be fed into the reactor at the same rate at which reaction products exit the vessel.

In alternative embodiments, the reaction is carried out for a period in the range of about 5 minutes to about 120 minutes, for example, in the range of between about 10 minutes to about 100 minutes, about 20 minutes to about 80 minutes, or about 30 minutes to about 40 minutes. The reaction time will depend on the selected reaction system and operating conditions and is generally sufficient to allow for the conversion of the reaction mixture to the desirable product mixture 4 without allowing for the production undesirable reaction products. At higher temperatures and pressures, the reaction time can be reduced.

When the feedstock and alcohol are reacted at, near or above the critical point of the alcohol, several simultaneous reactions can occur which allow for the subsequent isolation of the tocopherols and other product streams from the product mixture 4 using conventional methods which do not require additional reaction steps or complicated separation techniques. Following reaction product mixture 4 comprises free tocopherols, free sterols, fatty acid alkyl esters, and glycerol. The reactions that take place with each of the components of the reaction mixture are described in greater detail below.

In alternative embodiment, a reaction is carried out as a two-phase process involving a first hydrolysis stage using water, and a second hydrolysis stage using alcohol. In this embodiment, in the hydrolysis stage, water is mixed with the tocopherol-comprising feedstock and placed in a reactor. During this phase, any bound fatty acids, including glycerides (acylglycerols) and alcohol esters, e.g., tocopherol esters and sterol esters, are hydrolyzed to form a reaction slurry of free fatty acids, glycerine and free alcohols, including free tocopherols and sterols. Optionally, carbon dioxide is added during the first hydrolysis stage/phase.

In the second phase of the two-phase process, the second phase is an esterification phase, where the reaction slurry from the first hydrolysis phase is fed back into the reactor where it is mixed with alcohol. In alternative embodiments, following this reaction, the fatty acid alkyl esters (e.g., FAMEs), glycerols, unreacted alcohols and other products are separated from the tocopherols and sterols using e.g., distillation or other separation techniques.

Transesterification of Tocopherol and Sterol Esters:

Any esters present in the feedstock, including tocopherol esters and/or sterol esters, are transesterified with the alcohol. During transesterification, the fatty acid ester moiety of the ester is exchanged with the organic group of the alcohol to form a free phenol and an alkyl ester. For example, a supercritical reaction with tocopherol esters and methanol will yield free tocopherols and fatty acid methyl esters (FAME), also referred to as biodiesel. The foregoing reaction can be depicted as follows:

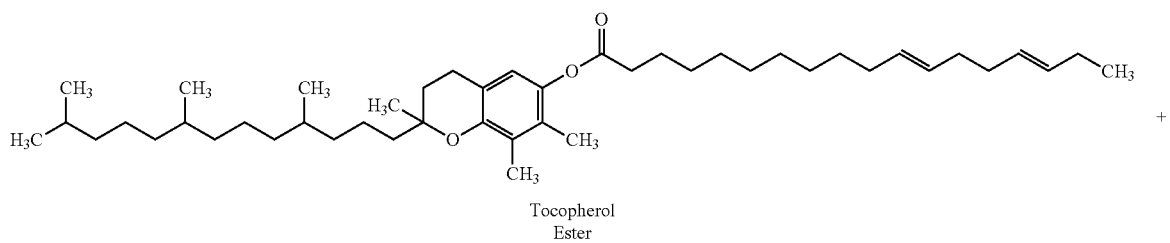

Tocopherol
Ester

+

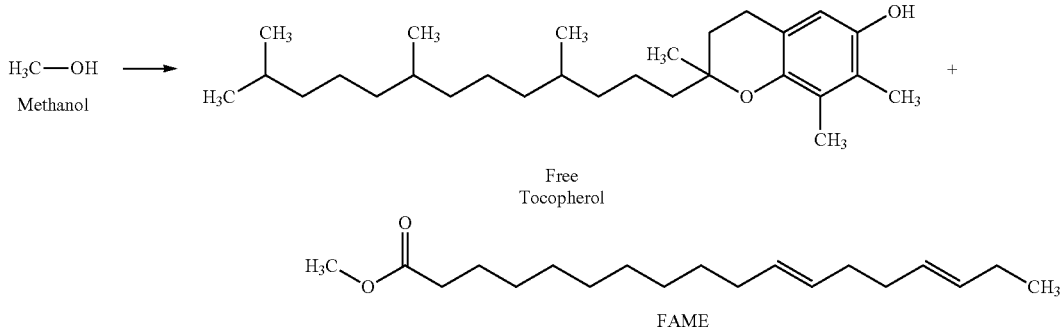

Similarly, a supercritical reaction with sterol esters and methanol will yield free sterols and fatty acid methyl esters (FAME), also referred to as biodiesel. The foregoing reaction can be depicted as follows:

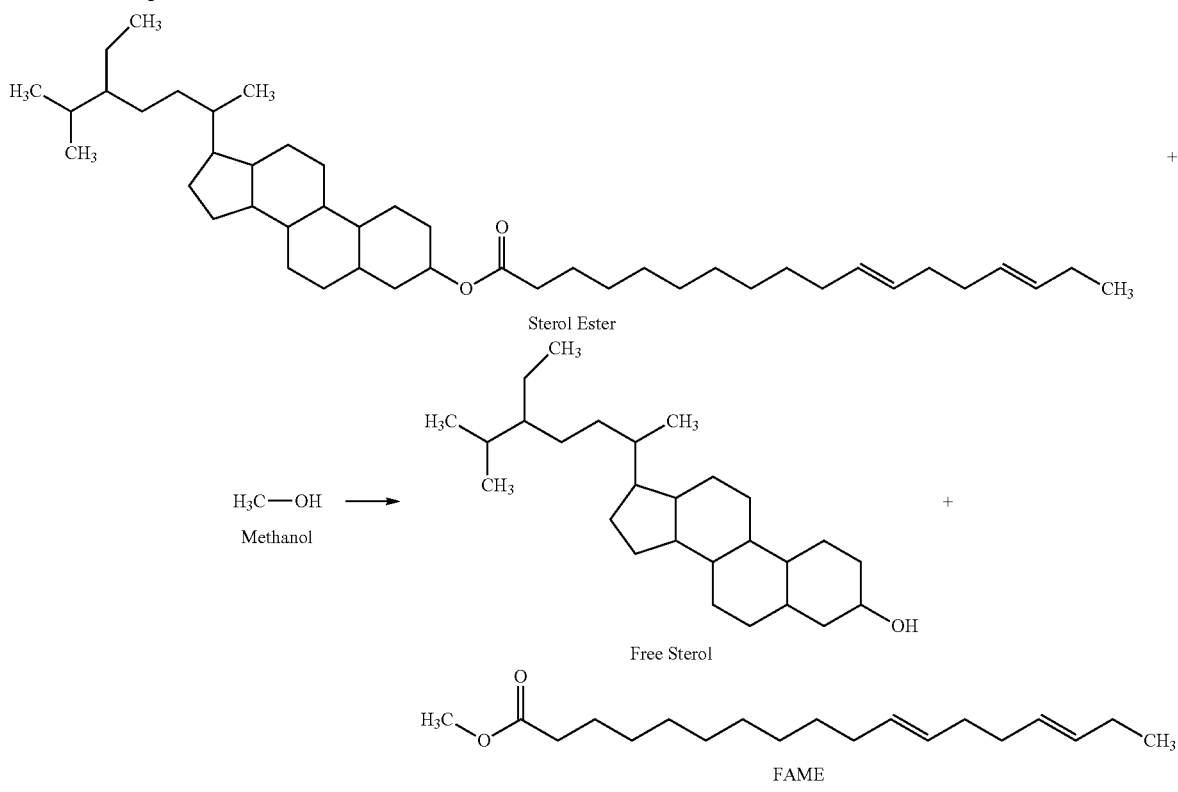

Transesterification of Glycerides:

Any glycerides present in the reaction mixture are transesterified to generate alkyl esters and glycerol. For example, if the alcohol in the embodiment is methanol, the glycerides present in the reaction mixture are converted to glycerol and FAME under the reaction conditions described herein. The forgoing reaction can be depicted as follows

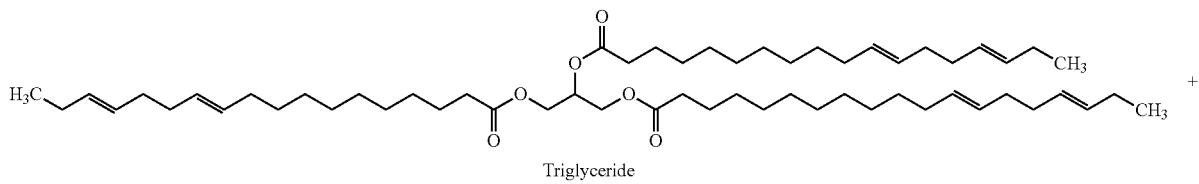

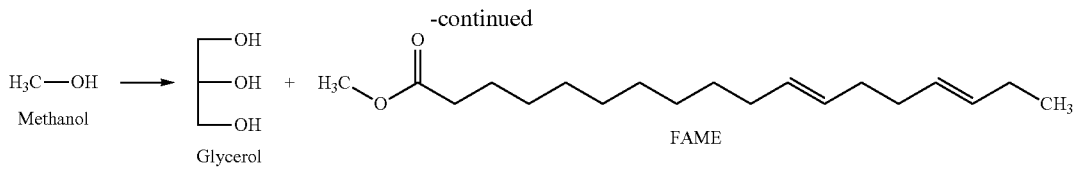

Esterification of Free Fatty Acids:

In various embodiments, the free fatty acids in the reaction mixture are esterified to form fatty acid alkyl esters. For example, if the alcohol in the embodiment is methanol, the free fatty acids are esterified to generate FAME (and water) under the reaction conditions described herein.

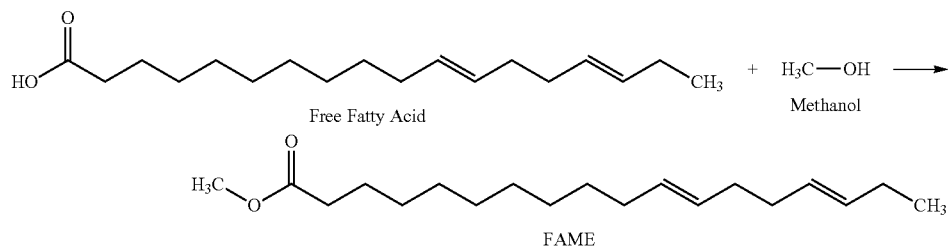

As can be seen from the reactions described above, and referring to FIG. 1 and FIG. 2, alternative embodiments of the present invention are able to convert a feedstock, e.g., a mixed lipid feedstock, 1 comprising primarily free tocopherols, free sterols, tocopherol and sterol esters, glycerides, and free fatty acids, to a product mixture 4 comprising primarily free tocopherols and free sterols, glycerol, and fatty acid alkyl esters. In alternative embodiments, the reaction conditions allow the free tocopherols and free sterols present in the reaction mixture to pass through the reactor vessel unchanged, generating a more uniform product mixture 4 and allowing for conventional separation techniques to be employed to isolate the free tocopherols from the other components of the product mixture.

Figure 3:
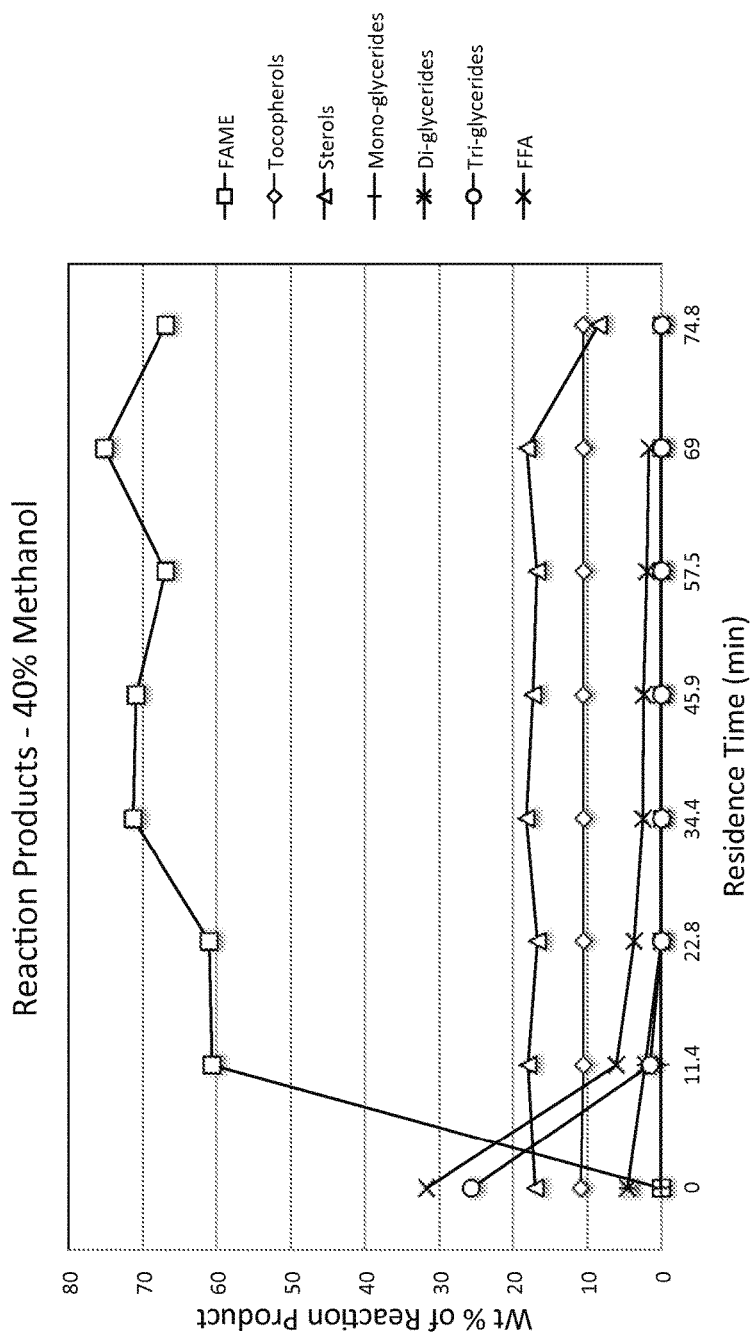
FIG. 3 is a graph showing an exemplary method of the invention for the production of FAME, the reduction of esters, and the non-reactivity of tocopherols and sterols in an exemplary method of the invention comprising reacting a soybean fatty acid distillate (SFAD) with 40% wt/wt supercritical methanol, as described below.

In alternative embodiments, the majority free fatty acids and glycerides are converted to fatty acid alkyl esters relatively quickly during the reaction, e.g. within the first 15 minutes of the reaction (see FIG. 3). Following the first approximately 15 minutes of the reaction, the remaining free fatty acids and glycerides are converted to FAME at a slower rate than during the first approximately 15 minutes of the reaction until substantially all of the free fatty acids and glycerides have been converted into FAME within the range of between about 50 minutes to about 75 minutes, e.g. between about 65 minutes and 70 minutes.

In alternative embodiments, referring to FIG. 2, the product mixture 4 can optionally be subjected to a liquid-vapor separation step in in which the mixture enters a suitable liquid-vapor separation unit or system, e.g. a flash separator 10, in which the mixture is heated to generate a vapor-phase 11 comprising any unreacted alcohol and optionally water, and a liquid phase 12 comprising the remaining reaction products, including the tocopherols. The vapor-phase 11 can optionally be condensed and subjected to an alcohol distillation step 13 in which the alcohol is separated from other components of the condensed vapor-phase 11, e.g. water 14. The distilled alcohol can optionally be recycled back 15 into the reactor for subsequent reactions 3.

Following the reaction or the optional liquid-vapor separation step, water-soluble 6 material, which can include, for example, water, glycerol, and a some amount of unreacted alcohol, can be selectively removed from the insoluble materials in the remaining product mixture 7 through conventional methods known in the art, for example, a counter-current water wash 5. In certain embodiments, for example, glycerol is removed from the product mixture using any number of known water washing techniques. In certain embodiments, the water-soluble 6 material is further subjected to an evaporation step (e.g., in a glycerol wiped film evaporator) 21 to generate a substantially purified glycerol product 10 and possibly an alcohol/water product 11 that can be sent to the distillation unit 13 for further separation into alcohol 15 suitable for recycling in the process and water 14. The purified glycerol 10 represents a valuable by-product in various embodiments of the present invention and can be converted to, for example, high-value products such as propylene glycol for sale in the antifreeze markets.

In alternative embodiments, the remaining water-insoluble components of the product mixture 7 (FIGS. 1 and 2) including tocopherols, are then selectively removed from the mixture in discreet fractions in the separation unit or system 8 (FIG. 1) through conventional means known in the art, e.g. fractional distillation, crystallization, chromatographic separation, ion exchange, or the like, or through an combination thereof. In certain embodiments, the water-insoluble material 7 is first subjected to a distillation step 22 (FIG. 2) wherein substantially all of the FAME 13 is removed. As illustrated in FIG. 2, the "bottoms" of the distillation column 14, comprising, the tocopherols, sterols, and optionally other residues and/or waxes, are subjected to a tocopherol separation step 23 wherein the tocopherols 9 and sterols 16 are separated into individual product streams.

By separating the water-insoluble fractions, free tocopherols are isolated in a marketable form. Further, each separated fraction represents a potentially valuable by-product. For example, in certain embodiments, the water-insoluble components of the product mixture are FAME, free tocopherols, and free sterols. FAME can be separated and sold into the global biodiesel markets. The free sterols may be used in a number of commercially valuable applications, e.g. as precursors to nutritional supplements.

The isolated tocopherols following separation are then available for use in high-value commercial applications, e.g.

as vitamin E supplements. In certain embodiments, the tocopherols are further isolated into discreet tocopherol or tocotrienol fractions, for example an alpha-tocopherol fraction. This step can be carried out by any of several known isolation techniques, for example chromatography, or ion exchange.

In alternative embodiments of the present invention, the isolation of free tocopherols from lipid mixtures can be achieved with only a single reaction step, without the use of any catalysts or acids and/or bases. Further, in alternative embodiments, the reaction conditions necessary to achieve a favorable product mixture are relatively mild and can be achieved without the use of capital-intensive equipment. These efficiencies also allow for the economic isolation of free tocopherols from mixed lipid feedstocks even if free tocopherols are present in very small quantities in the selected feedstock. This eliminates the need to aggregate large volumes of mixed lipid feedstocks in order to achieve the economies of scale needed for conventional tocopherol isolation methods.

Esterifying Organic Acids and Trans-Esterifying Esters in Mixed Lipid Feedstocks In alternative embodiments, the invention provides methods and industrial processes for esterifying organic acids and trans-esterifying esters in mixed lipid feedstocks comprising combining or feeding the mixed lipid feedstock with an alcohol to form a mixture, and then reacting the mixture at a temperature and pressure sufficient to cause the alcohol to become a supercritical or a near supercritical alcohol, i.e., reacting the mixture at a temperature and pressure sufficient to generate an alcohol at a supercritical state or an alcohol partially or substantially as a supercritical fluid, for a time sufficient to substantially esterify the organic acids and substantially transesterify the esters in the mixture, but leaving the free (unesterified) tocopherol and/or the free (unesterified) tocotrienol molecules substantially unesterified, and, if present, leaving the free (unesterified) sterols in the feedstock substantially unreacted (substantially unesterified).

In alternative embodiments of the methods and processes of the invention, after the supercritical reaction is completed (i.e., the reaction has substantially esterified the organic acids and substantially transesterified the esters in the mixture), where the reaction conditions can be, for example, at about 285° C. for about 35 minutes at about 1600 psi or in the range of between about 1700-2100 psig, or equivalent, and where that reaction can take place in a continuous flow reactor, such as a Plug Flow Reactor, or an equivalent reactor, the following steps can occur:

Heat Recovery:

The reacted material (i.e., the product mixture in which the organic acids are substantially esterified and the esters are substantially transesterified) is passed through another high pressure concentric heat exchanger wherein heat is withdrawn from the product mixture and optionally recovered (where the heat can be recycled for use elsewhere in the process, e.g. to heat the reactor, thereby decreasing the overall energy requirements of the system).

In alternative embodiments, the heat recovery is conducted under pressure, e.g. at approximately 50 psi below the pressure of the initial reaction, thus, the temperature of the product mixture from which heat is being transferred can be reduced to below the supercritical point of the solvent (e.g., methanol, which has a supercritical point of 240° C., so the heat is reduced to below 240° C.) while maintaining a pressure above its critical pressure (e.g. above about 1172 psi), thereby keeping the solvent, e.g., methanol, in a hot compressed liquid (non-vapor) state. In this alternative embodiment, the product mixture maintains a relatively thin (i.e. non-viscous) consistency, allowing for a high Log Mean Temperature Differential and Heat Transfer Coefficient, thereby reducing the total amount of contact area necessary to achieve the desired heat transfer.

In alternative embodiments, the reactor is heated using an oil, where optionally the oil can be heating by burning a natural gas, and the heat can be recovered by reducing the temperature of the product mixture from 285° C. to 215° C. (using the methanol as solvent example), or equivalent for other solvents, which allows a reduction in the amount of energy (e.g., natural gas) needed to heat the heating oil by approximately 30%.

In alternative embodiments the heat transfer process reduces the temperature of the product mixture to, e.g. about 215° C. for the methanol as an exemplary alcohol. By reducing the temperature, the subsequent flash separation step (see below) for the alcohol, e.g., methanol, recovery is less severe. A less severe flash results in less glycerol being removed from the product mixture in the same alcohol, e.g., methanol, recovery step, thereby allowing for maximum glycerol recovery in downstream glycerol recover step.

In alternative embodiments, the temperature of the reaction mixture is not lowered to a temperature such that a significant portion of the alcohol, e.g., methanol, remains with the other components of the product mixture during the alcohol, e.g., methanol, recovery step. For example, if the amount of heat recovered resulted in a reduction in temperature of the product mixture to about 180-190° C., the amount of methanol that remains with the product mixture following the alcohol (e.g., methanol) recovery step would be in the range of about 10 wt %. By maintaining a temperature of about 215° C., the amount of alcohol (e.g., methanol) remaining in the product mixture following the alcohol (e.g., methanol) recovery step is approximately 2 wt %.

Alcohol Recovery—Flash Process:

In alternative embodiments, following the heat recovery step, the product mixture undergoes a flash process wherein the product mixture is transferred to a flash drum or appropriate or equivalent vessel wherein the pressure is reduced to from the pressure within the heat exchanger, e.g. above 1171 psi or about 1200 psi, to, for example, about atmospheric pressure, or about less than 14 psi, e.g. less than 1 psi, or about 0.1 psi. The decrease in pressure results in an environment in which the vapor pressure of the alcohol, e.g., methanol, exceeds its external pressure (the pressure of the flash drum or vessel), allowing for the alcohol, e.g., methanol, and water (i.e. solvent) to vaporize or "flash" out of the product mixture.

A flash at 0.1 psi results in approximately 95% of the solvent present in the product mixture to vaporize and leave the flash vessel, with approximately 5% of the solvent remaining in a liquid state and existing the bottom of the flash unit along with the remaining products in the product mixture (i.e. the "ester stream"). In such embodiments, the concentration of solvent (i.e. alcohol/methanol and water) leaving the flash unit in a liquid state (in the ester stream) is approximately 2 wt. % of the ester stream.

In alternative embodiments, the ester stream leaves the flash unit at a temperature in the range of between about 110 to about 125° C., e.g. 115° C. and is sent to a heat exchanger, e.g. a standard shell and tube heat exchanger, wherein it is cooled to about 95° C. The recovered heat can be recycled for use in the process, e.g. to heat the reactor.

Alcohol Recycle—Distilling:

In alternative embodiments the alcohol/water (solvent), e.g., methanol/water, mixture that was flashed in a previous step, wherein the mixture is approximately 95 wt % methanol and 5 wt % water, is then distilled to yield a substantially pure alcohol, e.g., methanol product, e.g. approximately 99.8% or more alcohol, e.g., methanol. The substantially pure alcohol, e.g., methanol, product can be recycled to the alcohol, e.g., methanol supply, tank for use in subsequent reactions.

Glycerol Recovery/Water Wash

In alternative embodiments, after the ester stream is cooled via the heat exchanger, it is transferred to a static mixer wherein it is mixed with soft water in a ratio of about 50:1 ester stream-to-water by mass. The water and ester stream mixture is then transferred to a decanter wherein and oil (lipid) stream and an aqueous stream are formed and are separated.

The aqueous stream leaves the decanter comprises the alcohol, e.g., methanol, water (including water that was not removed in the flash separation step and water introduced in the present glycerol recovery/water-wash step) is then transferred to a glycerol stripping column, e.g. a 4-stage stripping column, in which the aqueous stream is introduced to the top of the column and, upon contacting the bottom of the column is heated such that a vapor phase, comprising primarily methanol and water, is generated and rises to the top of the column where it is removed. In this exemplary embodiment, the column "bottoms" are a primarily a glycerol product in the range about 80 to 88 wt % glycerol, e.g. about 85% glycerol, which can be marketed directly or upgraded to an USP grade tech glycerin.

In alternative embodiments, the contents of the separated vapor phase comprising water and glycerol will vary depending the composition of the starting feedstock. In one embodiment, e.g., in which soybean fatty acid distillate is the feedstock, the water/alcohol (e.g., methanol) product is approximately 55% alcohol (e.g., methanol) and 45% water. The alcohol (e.g., methanol)/water product is sent to the alcohol recovery unit wherein it is distilled to yield a substantially pure alcohol, e.g., methanol, product.

Recovering Tocopherols and Sterols from the Lipid Stream

In alternative embodiments, the lipid (oil) stream leaves the decanter with very small amounts of alcohol (e.g., methanol), water, and glycerol, e.g. 2000 ppm, 4000 ppm, and 150 ppm alcohol (e.g., methanol), water and glycerol, respectively. In order to remove some of the entrained water and alcohol (e.g., methanol) from the lipid stream, the lipid stream can be transferred from the decanter to a heating unit in which it is heated e.g. by a standard shell tube heat exchanger, to approximately 180° C. and flashed under low-pressure, e.g., under a pressure that is less than atmospheric pressure or is about less than 1 psi the water content of the lipid stream, where the pressure is reduced to about less than about 1000 ppm, e.g. less than about 400 ppm. The alcohol, e.g., methanol, and water removed in this step can be sent to the alcohol recycle unit wherein it is distilled to yield a substantially pure alcohol, e.g., methanol, product.

In alternative embodiments, the "dry" contents (the lipid stream having been flashed to remove additional water and methanol and comprised primarily of FAME and tocopherols and sterols) are then sent to an ester distillation column where the product is distilled to yield a tocopherol/sterol concentrate stream, e.g., comprising approximately 70% to about 100% tocopherols and sterols. In one embodiment, the ester distillation column is comprised of 4 stages of packing along with a spiral heat exchanger, and the distillation can occur at all under approximately 1 Torr of vacuum to prevent high temperatures and degradation of tocopherols.

The ester stream removed from ester the distillation, comprised primarily of FAME, can be marketed directly as a biodiesel fuel, or it can undergo further downstream processing in order to remove additional water and/or FFA such that it may be sold as "premium-grade" e.g. ASTM grade biodiesel. The "bottoms" stream (primarily tocopherols and sterols) leaving the ester distillation column can go onto further processing for to separate substantially all of the tocopherols from the sterols, yielding a substantially pure Vitamin E product.

The fatty acid alkyl esters produced in any of the embodiments of the invention can be used in a variety of commercial, pharmaceutical and industrial applications. For example, the fatty acid alkyl esters, e.g. fatty acid methyl esters, can be used directly as a fuel (e.g. as a biodiesel fuel) or a fuel additive. The fatty acid alkyl esters may also be subjected to one or more purification and/or separation procedures to generate individual "cuts" or streams of uniform fatty acid alkyl esters (i.e. alkyl esters of the same chemical structure). Theses "chemical" grade alkyl esters can be used in a variety of applications.

Sterols that have been isolated and/or purified in any of the embodiments of the invention can be used in a variety of industrial, pharmaceutical and commercial applications e.g. as a food additive, as an additive or component in thermoplastic resins, as a rate modifying agent in thermoplastic polymers, as a component in the production of liquid crystals, or as a pharmaceutical or a human nutritional supplement useful as, for example, a means of blocking cholesterol absorption.

The invention will be further described with reference to the following examples; however, it is to be understood that the invention is not limited to such examples.

EXAMPLES

Example 1

Esterification/Transesterification of Soybean Fatty Acid Distillate (SFAD) with Methanol This example describes an exemplary protocol of the invention:

A series of supercritical alcohol esterification/transesterification reactions of SFAD feedstock were conducted in order to determine optimum residence time and alcohol concentration for the simultaneous transesterification of glycerides and other esterified components (e.g. sterol esters, tocopherol esters), and simultaneous esterification of free fatty acids (FFA).

The SFAD feedstock was mixed with methanol in varying concentrations before entering a heated and pressurized continuous pipe-type, plug flow reactor (PFR). The reaction was allowed to run for several hours and samples were taken at regular intervals an analyzed to determine the rate of esterification/transesterification of the feedstock as indicated by the formation of fatty acid methyl esters (FAME) and a reduction in the percentage of glycerides and free fatty acids.

Prior to reaction, the methanol and SFAD were pumped and sheared through a Colloid mill for 15 minutes to form an emulsion. The reactor was simultaneously purged with nitrogen to remove any oxygen in the system 40% Methanol SFAD was reacted with methanol in a ratio of 60% SFAD to 40% methanol by weight. Operating conditions were defined as:

| | |
|---|---|
| SFAD (by wt. %) | 60 |
| MeOH (by wt. %) | 40 |
| Reactor Temperature (° C.) | 282 |
| Reactor Pressure (psi) | 1600 |
| Flow rate (gpm) | 0.75 |
| Target Res Time (min) | 75 |
| Expected Run Time (hrs) | 7 |

Table 1 shows the composition of the SFAD feedstock samples by % weight prior to reaction. Di- and tri-glyceride weight percentages were quantified using high-performance liquid chromatography (HPLC). Mono-glyceride, sterol, tocopherol, and FAME weight percentages were quantified using gas chromatography (GC). FFA weight percentage was quantified using titration.

TABLE 1

| Sample | FFA | FAME | Tocopherols | Sterols | Mono-glycerides | Di-glycerides | Tri-glycerides |
|---|---|---|---|---|---|---|---|
| 1 | 27.9 | 0 | 10.6 | 8.0 | 0 | 4.6 | 25.4 |
| 2 | 31.8 | 0 | 16.2 | 11.4 | 0 | 4.0 | 24.0 |
| 3 | 34.9 | 0 | 18.3 | 18.3 | 0.1 | 4.6 | 21.9 |

Portions of each of the three feedstock samples were then mixed with methanol in a ratio of 60% SFAD to 40% methanol and reacted in the operating conditions described above for a designated residence time. The composition of the resulting product mixture was then determined using the same analytical methods described above. Table 2 shows the composition of the product mixtures resulting from a series of reactions with increasing residence time using feedstock sample 1, by weight percentage.

TABLE 2

| Residence time (min) | FFA | FAME | Tocopherols | Sterols | Mono-glycerides | Di-glycerides | Tri-glycerides |
|---|---|---|---|---|---|---|---|
| 0.0 | 27.9 | 0 | 10.6 | 8.0 | 0 | 4.6 | 25.4 |
| 10.9 | 7.5 | 61.5 | 11.1 | 11.1 | 0.03 | 3.8 | 2.1 |
| 22.0 | 3.9 | 55.5 | 10.7 | 8.3 | 0.02 | 1.4 | 0 |
| 33.1 | 3.0 | 48.8 | 10.5 | 4.8 | 0.02 | 0 | 0 |
| 44.2 | 2.3 | 78.6 | 10.6 | 9.7 | 0.02 | 0 | 0 |
| 53.3 | 2.0 | 77.3 | 10.6 | 11.1 | 0 | 0 | 0 |
| 66.5 | 1.3 | 54.9 | 10.5 | 4.7 | 0 | 0 | 0 |

Table 3 shows the composition of the product mixtures resulting from a series of reactions with increasing residence time using feedstock sample 2, by weight percentage.

TABLE 3

| Residence time (min) | FFA | FAME | Tocopherols | Sterols | Mono-glycerides | Di-glycerides | Tri-glycerides |
|---|---|---|---|---|---|---|---|
| 0.0 | 31.8 | 0 | 16.2 | 11.4 | 0 | 4.0 | 24.0 |
| 12.0 | 7.4 | 42.4 | 16.2 | 11.3 | 0 | 1.4 | 1.8 |
| 23.5 | 4.1 | 51.5 | 16.0 | 12.4 | 0 | 0.2 | 0 |
| 35.3 | 2.8 | 58.9 | 16.1 | 12.9 | 0 | 0 | 0 |
| 47.4 | 1.8 | 59.5 | 16.1 | 14.8 | 0 | 0 | 0 |
| 59.7 | 1.6 | 65.8 | 16.1 | 13.4 | 0 | 0 | 0 |
| 71.8 | 1.5 | 60.6 | 16.3 | 9.5 | 0.01 | 0 | 0 |

Table 4 shows the composition of the product mixtures resulting from a series of reactions with increasing residence time using feedstock sample 3, by weight percentage.

TABLE 4

| Residence time (min) | FFA | FAME | Tocopherols | Sterols | Mono-glycerides | Di-glycerides | Tri-glycerides |
|---|---|---|---|---|---|---|---|
| 0.0 | 34.9 | 0 | 10.7 | 18.3 | 0.1 | 4.6 | 21.9 |
| 11.1 | 7.8 | 42.2 | 10.7 | 18.1 | 0.1 | 2.5 | 1.6 |
| 22.3 | 4.2 | 54.2 | 11.4 | 20.6 | 0.1 | 0.4 | 0 |
| 33.5 | 2.9 | 49.7 | 10.6 | 17.7 | 0.1 | 0 | 0 |
| 44.9 | 2.3 | 40.7 | 10.3 | 14.8 | 0.1 | 0 | 0 |
| 56.2 | 1.9 | 53.7 | 10.8 | 18.3 | 0.11 | 0 | 0 |
| 67.7 | 1.4 | 58.6 | 11.2 | 19.4 | 0.11 | 0 | 0 |
| 75.2 | 1.2 | 59.8 | 11.2 | 18.5 | 0.11 | 0 | 0 |

As shown in Tables 1-3, the majority (>75%) of FFA in all three samples was esterified to FAME within approximately the first 15 minutes of the reaction. Similarly, the majority of di- and tri-glycerides were transesterified to form FAME within the first approximately 35 minutes of the reaction.

As shown in FIG. 3, the near-complete reaction of glycerides and FFA in the SFAD feedstock to FAME took place within the first approximately 35 minutes of the reaction, in the above-stated reaction conditions. The majority of FAME production occurred early on in the reaction, and then proceeded at a slower rate towards maximum theoretical FAME yields for the feedstock samples.

30% Methanol

The above reactions were repeated with a 30% methanol mix, wherein SFAD was reacted with methanol in a ratio of 70% SFAD to 30% methanol by weight. Operating conditions were defined as:

| | |
|---|---|
| SFAD (by wt. %) | 70 |
| MeOH (by wt. %) | 30 |
| Reactor Temperature (° C.) | 282 |
| Reactor Pressure (psi) | 1600 |
| Flow rate (gpm) | 0.75 |
| Target Res Time (min) | 75 |
| Expected Run Time (hrs) | 7 |

Table 5 shows the composition of the SFAD feedstock samples by % weight prior to reaction. Di- and tri-glyceride weight percentages were quantified using high-performance liquid chromatography (HPLC). Mono-glyceride, sterol, tocopherol, and FAME weight percentages were quantified using gas chromatography (GC). FFA weight percentage was quantified using titration.

TABLE 5

| Sample | FFA | FAME | Tocopherols | Sterols | Mono-glycerides | Di-glycerides | Tri-glycerides |
|---|---|---|---|---|---|---|---|
| 1 | 31.7 | 0 | 10.5 | 17.0 | 0.1 | 4.6 | 25.6 |
| 2 | 37.7 | 0 | 10.6 | 17.8 | 0.1 | 5.2 | 27.7 |
| 3 | 31.7 | 0 | 10.6 | 20.4 | 0.1 | 6.09 | 26.4 |

Portions of each of the three feedstock samples were then mixed with methanol in a ratio of 70% SFAD to 30% methanol and reacted in the operating conditions described above for a designated residence time. The composition of the resulting product mixture was then determined using the same analytical methods described above. Table 6 shows the composition of the product mixtures resulting from a series of reactions with increasing residence time using feedstock sample 1, by weight percentage.

TABLE 6

| Residence time (min) | FFA | FAME | Tocopherols | Sterols | Monoglycerides | Diglycerides | Triglycerides |
|---|---|---|---|---|---|---|---|
| 0 | 31.7 | 0 | 10.9 | 17.0 | 0.06 | 4.6 | 25.6 |
| 11.4 | 6.1 | 60.6 | 10.5 | 18.0 | 0.06 | 2.2 | 1.5 |
| 22.8 | 3.7 | 61.0 | 10.5 | 16.7 | 0.06 | 0 | 0 |
| 34.4 | 2.5 | 71.3 | 10.5 | 18.2 | 0.06 | 0 | 0 |
| 45.9 | 2.4 | 70.9 | 10.6 | 17.3 | 0.06 | 0 | 0 |
| 57.5 | 2.0 | 66.9 | 10.5 | 16.8 | 0.06 | 0 | 0 |
| 69.0 | 1.7 | 75.2 | 10.5 | 18.1 | 0.06 | 0 | 0 |
| 74.8 | N/A | 66.9 | 10.6 | 8.5 | 0.06 | 0 | 0 |

Table 7 shows the composition of the product mixtures resulting from a series of reactions with increasing residence time using feedstock sample 2, by weight percentage.

TABLE 7

| Residence time (min) | FFA | FAME | Tocopherols | Sterols | Monoglycerides | Diglycerides | Triglycerides |
|---|---|---|---|---|---|---|---|
| 0 | 37.7 | 0 | 10.6 | 17.8 | 0.06 | 5.2 | 27.7 |
| 11.1 | 7.2 | 60.9 | 10.6 | 19.8 | 0.06 | 2.80 | 1.8 |
| 22.3 | 5.0 | 52.1 | 10.3 | 15.6 | 0.06 | 0.07 | 0 |
| 33.2 | 3.8 | 69.8 | 10.6 | 18.0 | 0.06 | 0 | 0 |
| 55.7 | 2.7 | 78.2 | 10.7 | 18.4 | 0.06 | 0 | 0 |
| 66.9 | 2.5 | 72.8 | 10.6 | 18.1 | 0.06 | 0 | 0 |
| 75.4 | 2.6 | 79.3 | 10.6 | 18.3 | 0.06 | 0 | 0 |

Table 9 shows the composition of the product mixtures resulting from a series of reactions with increasing residence time using feedstock sample 3, by weight percentage.

TABLE 8

| Residence time (min) | FFA | FAME | Tocopherols | Sterols | Monoglycerides | Diglycerides | Triglycerides |
|---|---|---|---|---|---|---|---|
| 0 | 31.7 | 0 | 10.6 | 20.4 | 0.06 | 6.1 | 26.4 |
| 11.9 | 6.9 | 46.3 | 10.6 | 22.0 | 0.06 | 3.0 | 2.1 |
| 22.1 | 4.3 | 53.7 | 10.7 | 21.0 | 0.06 | 0.9 | 0 |
| 33.1 | 2.6 | 51.9 | 10.6 | 20.6 | 0.06 | 0 | 0 |
| 44.1 | 2.1 | 54.2 | 10.6 | 20.5 | 0.06 | 0 | 0 |
| 55.1 | 2.2 | 56.2 | 10.6 | 20.7 | 0.06 | 0 | 0 |
| 66.2 | 2.2 | 61.4 | 10.7 | 22.3 | 0.06 | 0 | 0 |
| 74.5 | 2.1 | 62.4 | 12.0 | 20.4 | 0.06 | 0 | 0 |

Similar to the reactions comprising 40% methanol by weight, the majority of FFAs and glycerides in all three 30% methanol samples was converted to FAME within approximately the first 15 minutes of the reaction.

The concentration of sterols in both the 30% methanol and 40% methanol runs tended to increase slightly with increased residence time due to the conversion of sterol esters in the feedstock samples to free sterols. Tocopherol concentrations remained relatively constant as reaction residence time increased. This was due to a lack of tocopherol esters present in the feedstock, which would have been available for conversion to free tocopherols.

Example 2

Reaction Product Processing and Separation of Tocopherols and Sterols

This example describes an exemplary protocol of the invention:

Soybean fatty acid distillate (SFAD) was first reacted with supercritical methanol in a Plug Flow reactor at 285° C. and 1600 psi for 35 minutes. The Plug Flow reactor was heated with oil that surrounded the outer surface of the internal tube of the reactor (the internal tube was housed within an external tube, allowing the heated oil to flow between the inner surface of the external tube and the outer surface of the internal tube). The oil was heated using a natural gas-burning heater as a fuel source. The product mixture generated by the reaction was then subjected to several downstream processing steps in order to generate a mixture of primarily tocopherols and sterols that was essentially free of any ester products. The various processing steps are discussed in greater detail below.

Heat Recovery:

Following the reaction, the product mixture was transferred directly to a high-pressure concentric heat exchanger operating at 1620 psi. The reaction mixture was cooled to a temperature of 240° C. from a starting temperature of 285° C. By maintaining the pressure of the heat exchanger above the critical pressure of the methanol (1172 psi), the methanol remained in a hot-compressed liquid state, thereby remaining entrained in the reaction mixture and acting as a solvent. The solvent activity of the methanol allowed for a non-viscous reaction mixture with a high Log Mean Temperature Differential and Heat Transfer Coefficient as it was moved through the heat exchanger. As a result, the total amount of contact area required to reduce the temperature of the reaction mixture to 240° C. was kept to a minimum.

The captured heat was recycled to the reaction heater system, wherein it was used as a supplementary heat source for the reactor heating oil. By utilizing the recycled heat, the total amount of energy required to achieve the desired temperature of the reactor heating oil was reduced by approximately 30%.

Alcohol Recovery Using a Flash Drum:

Following heat recovery, the product mixture was then transferred to a flash drum under a pressure of 0.1 psi to recover the unreacted methanol. The drop in pressure of the product mixture in the heat recovery unit (approximately 1620 psi) to the pressure of the flash drum (0.1 psi) resulted in vaporization of the majority of both the water and methanol in the product mixture, as the vapor pressure of both water and methanol at the flash temperature (215° C.) exceeded their external pressures (i.e. the pressure in the flash drum). The flash resulted in the collection of approximately 95% of the total amount of methanol and water in the product mixture.

Upon entry into the flash drum, the product mixture was comprised of approximately 35 wt % water and methanol. The product stream ("ester stream") leaving the flash drum as bottoms was comprised of approximately 2 wt % water and methanol. The ester stream left the flash unit at approximately 115° C. and was transferred to a standard shell and tube heat exchanger wherein it was cooled to approximately 95° C. The captured heat was recycled as a supplementary heat source for heating the reactor heating oil.

Alcohol Distillation and Recycle

The methanol and water stream collected in the flash drum was comprised of approximately 90 wt % methanol and 5 wt % water. In order to obtain a high-purity methanol product that was suitable for recycling for use in subsequent reactions, the methanol/water stream was subjected to a simple distillation process in which a 99.8% methanol product was obtained. The purified methanol was transferred to the methanol supply tank for use in subsequent reactions.

Glycerol Recovery Using a Water-Wash

The cooled ester stream from the flash drum was transferred a static mixer wherein it was mixed with soft water in a ratio of 50:1 ester stream-to-water by mass. The mixture was then transferred to a decanter wherein a lipid phase (comprising primarily fatty acid methyl esters, tocopherols, sterols, and smaller amounts of additional products) and an aqueous phase (comprising water, glycerol, and methanol) were formed. The aqueous phase was transferred to a 4-stage stripping column to recover the glycerol. The aqueous stream entered the top of the stripper and was heated when it reached the bottom of the column, generating a vapor phase comprising water and methanol in a ratio of approximately 55% methanol to 45% water. The vapor phase was collected and transferred to the alcohol recovery unit for distillation (see the "Alcohol Recovery" step above) wherein a methanol product of approximately 99.8% purity was obtained.

The bottoms of the stripper column were comprised of approximately 85% glycerol suitable for direct sale or upgrading to produce a USP grade tech glycerin.

Tocopherol and Sterol Recovery

The lipid phase collected from the decanter comprised small amounts of entrained methanol, water and glycerol in the amounts of 2000 ppm, 4000 ppm, and 150 ppm, respectively. In order to reduce the quantities of methanol and water, the lipid phase was transferred to heating unit in which it was heated to approximately 180° C. and flashed under 50 Torr. The vapor phase resulting from the flash, comprising methanol and water, was sent to the alcohol recovery unit for distillation (see the "Alcohol Recovery" step above) wherein it a methanol product of approximately 99.8% purity was obtained.

The "dry" contents following the flash were comprised primarily of FAME, tocopherols, and sterols, with a water content of approximately 400 ppm. This product stream was transferred to a distillation column comprised of 4 packing stages and a spiral heat exchanger wherein the product stream was distilled in order to separate the FAME in the product stream from the tocopherols and sterols. The product stream was distilled under 1 Torr of vacuum in order to alleviate the need for a high-temperature distillation that would potentially degrade the tocopherols. The distilled FAME product was suitable for direct use as a biodiesel fuel.

The tocopherol/sterol stream obtained in the distillation step was comprised of approximately 95% tocopherols and sterols.

While the forgoing written description of the invention enables one of ordinary skill to make and use what is considered presently to be the best mode thereof, those of ordinary skill will understand and appreciate the existence of variations, combinations, and equivalents of the specific embodiments, methods, and examples herein. The invention should therefore not be limited by the above described embodiments, methods and examples, but by all embodiments and methods within the scope and spirit of the invention.

What is claimed is:

1. A method or an industrial process for isolating free or unesterified tocopherols and/or free or unesterified tocotrienols from a mixed lipid feedstock, the method comprising:
    (a) providing the mixed lipid feedstock comprising unesterified or free tocopherol and/or unesterified tocotrienol molecules, and esters of fatty acids, and optionally further comprising a free or unesterified sterol, a sterol ester, a glyceride, a hydrocarbon, or a free fatty acid; and
    (b) combining or feeding the mixed lipid feedstock with an alcohol to form a mixture;
    (c) reacting the mixture at a temperature and pressure sufficient to cause the alcohol to become supercritical or near supercritical alcohol or to generate an alcohol at a supercritical state or an alcohol partially or substantially as a supercritical fluid, thereby substantially esterifying the organic acids and substantially transesterifying the esters in the mixture of step (b), but leaving the free or unesterified tocopherol and/or the free or unesterified tocotrienol molecules substantially unreacted or substantially unesterified,
    and, if present, leaving the free or unesterified sterols in the mixed lipid feedstock substantially unreacted or substantially unesterified,
    thereby generating a reacted reaction mixture comprising reaction products comprising unesterified or free tocopherol and/or tocotrienol molecules, and if present, unesterified or free sterols, and fatty acid alkyl esters,
    wherein: substantially all of the organic acids are esterified, and substantially all of the tocopherol and/or tocotrienol molecules are unesterified, and if sterols are present, substantially all of the sterols are unesterified; and
    (d) separating, isolating, or purifying the reaction products in the reacted reaction mixture by distillation to generate a product stream comprising the free or unesterified tocopherols and/or free or unesterified tocotrienols,
    wherein the distillation is done under conditions comprising a vacuum in order to alleviate the need for a high-temperature distillation that would potentially degrade the tocopherols,
    and the product stream is comprised of at least about 95% free or unesterified tocopherols and/or free or unesterified tocotrienols.

2. The method or industrial process of claim 1, wherein the free or unesterified sterol, the sterol ester, the free fatty acid, the glyceride, optionally mono-, di-, and/or triglyceride, or the hydrocarbon are separated, isolated or purified into separate fractions or discreet fractions, wherein optionally the hydrocarbon comprises squalene.

3. The method or industrial process of claim 1, wherein:
    (a) the mixed lipid feedstock of step (a) comprises a vitamin E, an unesterified tocopherol or tocotrienol, an ester of the tocopherol or tocotrienol, or any combination thereof;
    (b) the mixed lipid feedstock of step (a) comprises free or unesterified tocopherols, free or unesterified tocotrienols, tocopherol esters, tocotrienol esters, free sterols, sterol esters, free fatty acids, a glyceride hydrocarbons, or any combination thereof,
    wherein optionally the hydrocarbon comprises a squalene or the glyceride comprises a mono-, di-, or a triglyceride;

(c) the mixed lipid feedstock of step (a) comprises: unesterified tocopherol or tocotrienol molecules in the range of between about 0.5% and 35 wt % of the mixed lipid feedstock, or about 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29% or 30% or more wt %, of the mixed lipid feedstock;

(d) the reacting of the mixture of step (c) is under conditions comprising a temperature in a range of between about 100° C. and about 350° C. and a pressure in a range of between about 500 psi to about 3000 psi;

(e) the reacting of the mixture of step (c) is under conditions comprising reacting for a time period in a range of between about 0 minutes to about 120 minutes, or between about 1 to 100 minutes;

(f) the alcohol has between 1 and 5 carbons, or the alcohol has 1, 2, 3, 4, 5, 6, or 7 or more carbons;

(g) the alcohol comprises a methanol, an ethanol, a butanol, an isopropyl alcohol, a sec-butanol, a t-butanol, a benzyl alcohol, or a combination thereof, (h) the mixed lipid feedstock comprises a deodorizer distillate, or a vegetable oil deodorizer distillate or a distillate of a vegetable oil deodorization process;

(i) the method or industrial process of (h), wherein the deodorizer distillate or distillate of the vegetable oil deodorization process is derived from a soybean oil, a canola oil, a rapeseed oil, a sunflower oil, a rice bran oil, an algae oil, a jatropha oil, a corn oil, a camelina oil, or a safflower oil;

(j) the mixed lipid feedstock comprises a fatty acid distillate; or (k) the method or industrial process of (j), wherein the fatty acid distillate is derived from palm oil.

4. A method or industrial process for recovering or separating free or unesterified tocopherols, free or unesterified tocotrienols, or both, from a mixed lipid feedstock, the method or industrial process comprising:

(a) combining the mixed lipid feedstock with an alcohol to form a reaction mixture, wherein the mixed lipid feedstock comprises free or unesterified tocopherols and/or free or unesterified tocotrienols, sterols, free fatty acids and glycerides, and optionally the mixed lipid feedstock further comprises tocopherol and/or tocotrienol esters and sterol esters, or any combination thereof;

(b) forming a reacted reaction mixture comprising a reaction product mixture by reacting the reaction mixture:

(1) at a temperature in the range of between about 100° C. and about 350° C., and at a pressure in the range of between about 500 psi to about 3000 psi, or, the mixture is reacted at a pressure slightly in excess of a vapor pressure of the alcohol at a selected operating temperature, and optionally the pressure is about 1, 2, 3, 4, 5, 6, 7, 8, 9, 10, 11, 12, 13, 14, 15, 16, 17, 18 19 or 20 psi or more, or the pressure is between about 5 to 50 psi or more, or the pressure is over the vapor pressure of the alcohol; or (2) at a temperature and pressure sufficient to generate a supercritical or near supercritical alcohol or when the alcohol reaches a supercritical state or partially or substantially becomes a supercritical fluid; thereby:

i. converting substantially all of the tocopherol esters and/or tocotrienol esters to generate a reaction product mixture comprising free or unesterified tocopherols and/or free or unesterified tocotrienols, and fatty acid alkyl esters, ii. converting the sterol esters to generate a reaction product mixture comprising sterols and fatty acid alkyl esters, iii. converting the glycerides to generate a reaction product mixture comprising fatty acid alkyl esters and glycerol, iv. converting the free fatty acids to generate a reaction product mixture comprising fatty acid alkyl esters; and v. leaving the free or unesterified tocopherols, free or unesterified tocotrienols and, if present, free or unesterified sterols in the mixed lipid feedstock substantially unreacted or substantially unesterified, thereby generating a reaction product mixture comprising reaction products comprising: free or unesterified tocopherols and/or free or unesterified tocotrienols, free or unesterified sterols, and fatty acid alkyl esters;

(c) transferring the reaction product mixture of (c) to a heat exchanger under pressure and cooling the reaction mixture;

(d) transferring the cooled reaction mixture of (d) to a flash drum and dropping the pressure to vaporize methanol or water in the cooled reaction mixture, and remove the vaporized methanol or water, thereby generating a cooled mixture comprising fatty acid methyl esters, free or unesterified tocopherols, free or unesterified tocotrienols, and sterols;

(e) mixing the cooled mixture of (d) with water to form a lipid phase comprising the fatty acid methyl esters (FAME), free or unesterified tocopherols, free or unesterified tocotrienols, and sterols, and an aqueous phase comprising water, glycerol and methanol;

(f) removing the lipid phase of (e) and heating under pressure to create a vapor phase comprising methanol and water, and removing the vapor phase from the lipid phase; and (g) transferring the lipid phase of (f) to a distillation column, and distilling in a vacuum to separate the FAME from the free or unesterified tocopherols and/or free or unesterified tocotrienols, thereby recovering or separating the free or unesterified tocopherols, free or unesterified tocotrienols, or both, from the mixed lipid feedstock.

5. The method or industrial process of claim 4, wherein:

(a) the mixed lipid feedstock comprises free tocopherols, free tocotrienols, tocopherol esters, tocotrienol esters, free sterols, sterol esters, free fatty acids, a glyceride hydrocarbons, or any combination thereof, wherein optionally the hydrocarbon comprises a squalene or the glyceride comprises a mono-, di-, or a triglyceride;

(b) the mixed lipid feedstock comprises tocopherols and/or tocotrienols in a range of between about 0.5% to about 30 wt %, or about 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29% or 30% or more wt %, of the mixed lipid feedstock;

(c) the reaction product mixture comprises free tocopherols, free tocotrienols, free sterols, fatty acid alkyl esters, glycerol, squalene, or any combination thereof;

(d) the reaction mixture is reacted at a temperature in the range of between about 150° C. and about 300° C., or in a range of between about 100° C. and about 350° C., and a pressure in the range of between about 500 psi to about 3000 psi;

(e) the reaction mixture is reacted for a time period in a range of between about 0 minutes to about 120 minutes, or between about 1 minute and about 100 minutes;

(f) the alcohol has between 1 and 5 carbons, or the alcohol has 1, 2, 3, 4, 5, 6, or 7 or more carbons;

(g) the alcohol is a methanol, an ethanol, a butanol, an isopropyl alcohol, a sec-butanol, a t-butanol, a benzyl alcohol, or a combination thereof;

(h) the mixed lipid feedstock comprises a deodorizer distillate, or a vegetable oil deodorizer distillate or a distillate of a vegetable oil deodorization process;

(i) the method or industrial process of (h), wherein the deodorizer distillate or distillate of a vegetable oil deodorization process is derived from a soybean oil, a canola oil, a rapeseed oil, a sunflower oil, a rice bran oil, a safflower oil or a mixture thereof;

(j) the mixed lipid feedstock is a fatty acid distillate; or (k) the method or industrial process of (I), wherein the fatty acid distillate is derived from a palm oil.

6. The method or industrial process of claim 1, wherein the tocopherol comprises alpha-tocopherol, beta-tocopherol, gamma-tocopherol, delta-tocopherol or a combination thereof, and optionally the tocotrienol comprises alpha-tocotrienol, beta-tocotrienol, gamma-tocotrienol, delta-tocotrienol or a combination thereof.

7. The method or industrial process of claim 1, wherein in step (b) the alcohol comprises at least about 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, or 40% or more wt %, of the mixed lipid feedstock, or between about 0.5% and 50% wt %, of the mixed lipid feedstock, or between about 1% and 40% wt %, of the mixed lipid feedstock, or, the amount of alcohol in the mixture can be in the range of between about 1 mol to about 100 mol per mol of the mixed lipid feedstock, or between about 10 mol to about 90 mol per mol of the mixed lipid feedstock, about 20 mol to about 80 mol per mol of the mixed lipid feedstock, about 30 mol to about 70 mol per mol of the mixed lipid feedstock, or about 40 mol to about 60 mol per mol of the mixed lipid feedstock.

8. The method or industrial process of claim 1, wherein in step (b) the combining or feeding step comprises feeding the mixture into a reactor or a reaction vessel as a continuous process, and optionally the reactor or reaction vessel is purged with nitrogen prior to the mixed lipid feedstock and alcohol entering the reactor.

9. The method or industrial process of claim 1, wherein alcohol comprises methanol and the fatty acid alkyl esters comprise fatty acid methyl esters (FAME).

10. The method or industrial process of claim 1, wherein the reaction mixture comprises reaction products and unreacted products comprising free sterols, sterol esters, free fatty acids, glycerides, hydrocarbons or any combination thereof, wherein optionally the hydrocarbon comprises squalene.

11. The method or industrial process of claim 1, wherein the glyceride comprises a mono-, di-, and/or tri-glyceride.

12. The method or industrial process of claim 1, wherein the mixture is reacted at a temperature in a range of between about 150° C. and about 300° C., or in a range of between about 100° C. and about 350° C.

13. The method or industrial process of claim 1, wherein the mixture is reacted at a pressure in the range of between about 500 psi to about 3000 psi, or, the mixture is reacted at a pressure slightly in excess of a vapor pressure of the alcohol at a selected operating temperature, and optionally the pressure is about 1, 2, 3, 4, 5, 6, 7, 8, 9, 10, 11, 12, 13, 14, 15, 16, 17, 18 19 or 20 psi or more, or between about 5 to 50 psi or more, over the vapor pressure of the alcohol.

14. The method or industrial process of claim 1, wherein at least about 90% of the organic acids are esterified, and at least about 90% of the tocopherol and/or tocotrienol molecules are unesterified, and if sterols are present, at least about 90% of the sterols are unesterified.

15. The method or industrial process of claim 2, wherein:

(a) the separated, isolated or purified free tocopherols or free tocotrienols comprise one, several or all of the four tocopherols or four tocotrienols, and optionally one or more of the four tocopherols comprise an alpha, beta, gamma, or delta tocopherol, or one or more of the four tocotrienols comprise an alpha, beta, gamma, or delta tocotrienol.

16. The method or industrial process of claim 1, wherein the alcohol comprises at least about 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, or 40% or more wt %, of the mixed lipid feedstock, or between about 0.5% and 50% wt %, of the mixed lipid feedstock, or between about 1% and 40% wt %, of the feedstock, or, the amount of alcohol in the mixture can be in the range of between about 1 mol to about 100 mol per mol of the mixed lipid feedstock, or between about 10 mol to about 90 mol per mol of the mixed lipid feedstock, about 20 mol to about 80 mol per mol of the mixed lipid feedstock, about 30 mol to about 70 mol per mol of the mixed lipid feedstock, or about 40 mol to about 60 mol per mol of the mixed lipid feedstock.

17. The method or industrial process of claim 1, wherein the vacuum used in step (d) is about 1 Torr of vacuum.

18. The method or industrial process of claim 4, wherein the vacuum used in step (g) is about 1 Torr of vacuum.

19. The method or industrial process of claim 3, wherein in step (d), the temperature is in a range of between about 150° C. and about 300° C.

20. The method or industrial process of claim 4, wherein in step (b)(1) the temperature is in the range of between about 150° C. to about 300° C., and the a pressure is in the range of between about 1,000 psi to about 3,000 psi.

* * * * *